United States Patent [19]
van der Linde et al.

[11] Patent Number: 4,704,232
[45] Date of Patent: Nov. 3, 1987

[54] FLAVOURING AND PERFUME COMPOSITIONS, FLAVOURED FOODSTUFFS AND LUXURY CONSUMABLES AND PERFUMED PRODUCTS WHICH CONTAIN ONE OR MORE SPATHULENOLS AS THE BASE MATERIAL, A SPATHULENOL DERIVATIVE AND A PROCESS FOR THE PREPARATION OF SPATHULENOLS

[75] Inventors: Leendert M. van der Linde; Franciscus P. van Lier; Antonius J. A. van der Weerdt, all of Huizen, Netherlands

[73] Assignee: Naarden International N.V., Ussum, Netherlands

[21] Appl. No.: 675,197

[22] Filed: Nov. 27, 1984

[30] Foreign Application Priority Data

Nov. 28, 1983 [NL] Netherlands ............... 8304073

[51] Int. Cl.$^4$ ............... A61K 7/46; C11B 9/00; C07C 35/22
[52] U.S. Cl. ........................... 512/19; 568/817
[58] Field of Search ............ 252/522 R; 568/817

[56] References Cited

U.S. PATENT DOCUMENTS 3,660,489  5/1972  Lamparsky et al. ............ 568/817
4,535,192  8/1985  Hall et al. ............ 252/522 R

FOREIGN PATENT DOCUMENTS 0858832  8/1981  U.S.S.R. ............ 568/817

OTHER PUBLICATIONS

Chan et al., "J. Org. Chem.", vol. 39, No. 22, pp. 3261+ (1974).
R. C. Bowyer and P. R. Jefferies, Chem. Ind., 1963, p. 1245.
S. M.-K., Juell et al., Arch Pharm., 309, 1976, pp. 458-466.
C. Fratinni et al., Z. Lebensm.-Unters. Forsch., 172, 1981, No. 6, pp. 457-459.
F. Chialva et al., Riv. Ital. Essenze Profumi Piante Off., 63, 1981, No. 7, pp. 350-352.
O. Mott et al., Arch. Pharm., 311, 1978, No. 1, pp. 75-76.
M. Repcak et al., Biol. Plant., 22, 1980, No. 6, pp. 420-427.
D. Joulain et al., Riv. Ital. Essenze Profumi Piante Off., 58, 1976, pp. 129-131 and 479-485.
R. Kaiser et al., J. Agric. Food. Chem., 23, 1975, No. 5, pp. 943-950.
H. Surburg and A. Mondon, Chem Ber., 114, 1981, pp. 118-130.
S. Arctander, Perfume and Flavor Chemicals, Montclair, New Jersey, 1969.
S. Arctander, Perfume and Flavor Materials of Natural Origin, Elizabeth, N.J., 1960.
T. E. Furia et al., CRC Fenaroli's Handbook of Flavor Ingredients, 2nd edition, Cleveland, CRC Press Inc., 1975.
Houben-Weyl, Methoden der Organischen Chemie, vol. VII-2b, pp. 1292-1300.
Z. Cohen et al., J. Org. Chem., 40, 1975, pp. 2141-2142.
H. O. House, Modern Synthetic Reactions, 2nd edition, pp. 682-709.
C. Beecham and C. Djerassi, Tetrahedron, 34, 1978, pp. 2503-2508.
Bruno Maurer et al., "New Sesquiterpenoids from Clary Sage Oil (Salvia sclarea L.)", Helvetica Chimica Acta, vol. 66, No. 220, Nov. 2, 1983, pp. 2223-2235.
Horst Surburg et al., "Synthese von (−)-Spathulenol", Chemische Berichte, vol. 114, 1981.
Z. Cohen et al., "Dry Ozonation. A Method for Stereoselective Hydroxylation of Saturated Compounds on Silica Gel", Journal of Organic Chemistry, vol. 40, No. 14, 1975, pp. 2141-2142.
S. Juell et al., "New Substances Isolated from the Essential Oils of Various Artemisia Species, Part 1 Spathulenol, an Azulenic Sesquiterpene Alcohol", Chemical Abstracts, vol. 85, No. 3, 68120z.

Primary Examiner—Werren B. Lone
Attorney, Agent, or Firm—Brumbaugh, Graves Donohue & Raymond

[57] ABSTRACT

Flavouring and perfume compositions, flavoured foodstuffs and luxury consumables and perfumed products which contain (+)-spathulenol and/or (+)-4a-allospathulenol, having respective structural formulae

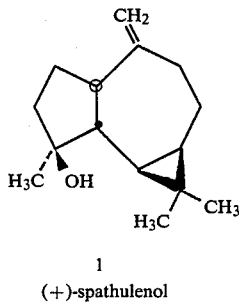 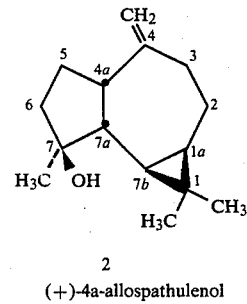

1
(+)-spathulenol 2
(+)-4a-allospathulenol as the base material (+)-4a-allospathulenol per se and a process for the preparation of these spathulenols.

13 Claims, No Drawings

FLAVOURING AND PERFUME COMPOSITIONS, FLAVOURED FOODSTUFFS AND LUXURY CONSUMABLES AND PERFUMED PRODUCTS WHICH CONTAIN ONE OR MORE SPATHULENOLS AS THE BASE MATERIAL, A SPATHULENOL DERIVATIVE AND A PROCESS FOR THE PREPARATION OF SPATHULENOLS

The invention relates to flavouring and perfume compositions which contain one or more spathulenols as the base material, and to foodstuffs and luxury consumables flavoured with, and products perfumed with, one or more of these compounds or with the said compositions. The invention moreover relates to a spathulenol derivative and to a process for the preparation of spathulenols.

There is a continued demand for the preparation of synthetic flavourings and fragrances and the use thereof in foodstuffs, drinks, pharmaceuticals, tobacco and the like and in products to be perfumed, such as cosmetics, soaps, detergents, household products and the like. This demand is stimulated by the inadequate amount and often varying quality of natural flavourings and fragrances.

(+)-Spathulenol was first of all reported in the ethereal oil of *Eucalyptus spathula* (R. C. Bowyer and P. R. Jefferies, Chem. Ind. 1963, page 1245), and subsequently in ethereal oils of various other plants, of which some are used on a limited scale as a base material for the flavouring and perfume industry.

(+)-Spathulenol has been found in various types of Artemisia, see, for example, S. M.-K, Juell et al., Arch. Pharm. 309 (1976), 458–66, C. Fratinni et al., Z. Lebensm.—Unters. Forsch. 172 (1981), No. 6, 457–9 and F. Chialva et al., Riv. Ital. Essenze Profumi Piante Off. 63 (1981), No. 7, 350–2; in camomile (*Matricaria chamomilla*), see for example O. Mott et al., Arch. Pharm. 311 (1978), No. 1, 75–6 and M. Repcák et al., Biol. Plant. 22 (1980), No. 6, 420–27; in hyssop (*Hyssopus officinalis*), see for example D. Joulain et al., Riv. Ital. Essenze Profumi Piante Off. 58 (1976), 129–31 and 479–85. The compound was also found in buchu leaf oil by R. Kaiser et al., J. Agric. Food. Chem. 23 (1975), No. 5, 943–50, in the course of their investigation of the organoleptically important components of this oil. They report that a small number of the many compounds found by them make an important contribution to the organoleptic properties of buchu leaf oil; however, spathulenol is not amongst these. S. M.-K. Juell et al., simply report that (+)-spathulenol has an earthy-aromatic odour and a bitter herbal flavour but give no indications concerning the usefulness of this compound as a flavouring or fragrance. Further, no data whatsoever are to be found in the literature concerning the organoleptic properties of this compound, concerning its possible usefulness as a flavouring or fragrance, or concerning a possible contribution to the organoleptic properties of the ethereal oils in which it occurs.

(+)-Spathulenol has hitherto never been prepared synthetically. Recently H. Surburg and A. Mondon in Chem. Ber. 114 (1981) 118'130 have described an 18-stage synthesis of (−)-spathulenol starting from (−)-β-pinene with an overall yield of about 0.2%.

Surprisingly, it has now been found that (+)-spathulenol and (+)-4a-allospathulenol, having respective structural formulae

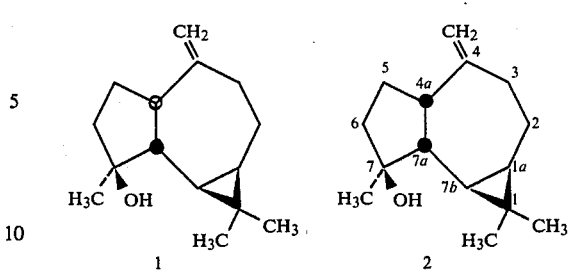

possess valuable organoleptic properties. They both have a dry woody odour somewhat reminiscent of cascarilla, and a flavour which in some respects is reminiscent of cassia. Though (+)-spathulenol, as reported, occurs in various ethereal oils, 4a-allospathulenol has hitherto not been described in the literature.

The compounds according to the invention can be used as flavourings or fragrances as they are, or can first be mixed with suitable carriers or diluents. They can also be combined with other individual compounds or with mixtures, for example with ethereal oils, in the manner customary for the preparation of flavouring compositions or perfume compositions. By the terms "flavouring composition" and "perfume composition" there are here respectively meant mixtures of flavourings and fragrances and/or ethereal oils, if desired dissolved in a suitable solvent or mixed with a pulverulent substrate as well as converted to a pulverulent product, and used in order to impart a desired flavour or odour to all sorts of products, or to intensify or improve the flavour or odour which these products already possess. Products to be flavoured are foodstuffs and luxury consumables, by which there are here understood solid or liquid products intended for human consumption including also tobacco products, medicines and toothpastes. Products to be perfumed are, for example, soap, detergents, cleaners and other household products, cosmetics and body care products.

Since (+)-spathulenol occurs as a constituent in various ethereal oils, the use of (+)-spathulenol in this form falls outside the scope of the invention; the use of (+)-spathulenol which is isolated from products of plant origin and is then used as a flavouring or a fragrance on the other hand does fall within the scope of protection of the invention.

Perfume and flavouring base materials which can advantageously be combined with the compounds according to the invention are given, for example, in S. Arctander, Perfume and Flavor Chemicals (Montclair, N.J., 1969); in S. Arctander, Perfume and Flavor Materials of Natural Origin (Elizabeth, N.J., 1960) and in the T. E. Furia et al., CRC Fenaroli's Handbook of Flavor Ingredients 2nd ed. (Cleveland, CRC Press Inc. 1975).

The quantities to be used of the compounds according to the invention can differ greatly and depend inter alia on the product wherein the compounds are used and on the nature and quantity of the other components of a flavouring or perfume composition. In most cases, an amount of 0.1 part by weight per thousand million of a compound according to the invention in foodstuffs and luxury consumables will already be clearly perceptible. In concentrated flavouring compositions, a quantity of 1% by weight or even more can in some cases be used advantageously.

In concentrated perfume compositions, quantities of 1 part by weight per million can have a distinctly perceptible effect on the scent impression. On the other hand, to achieve special odour effects it is also possible to use a quantity of 10% by weight or even more in a composition. In products perfumed with the aid of perfume compositions these concentrations are proportionately lower, depending on the quantity of composition used in the end product.

Surprisingly, spathulenol and its stereoisomers can be prepared in a relatively simple manner in accordance with a three-stage synthesis starting from aromadendrene and/or allo-aromadendrene, as is shown for (+)-spathulenol and (+)-4a-allospathulenol in the following reaction scheme

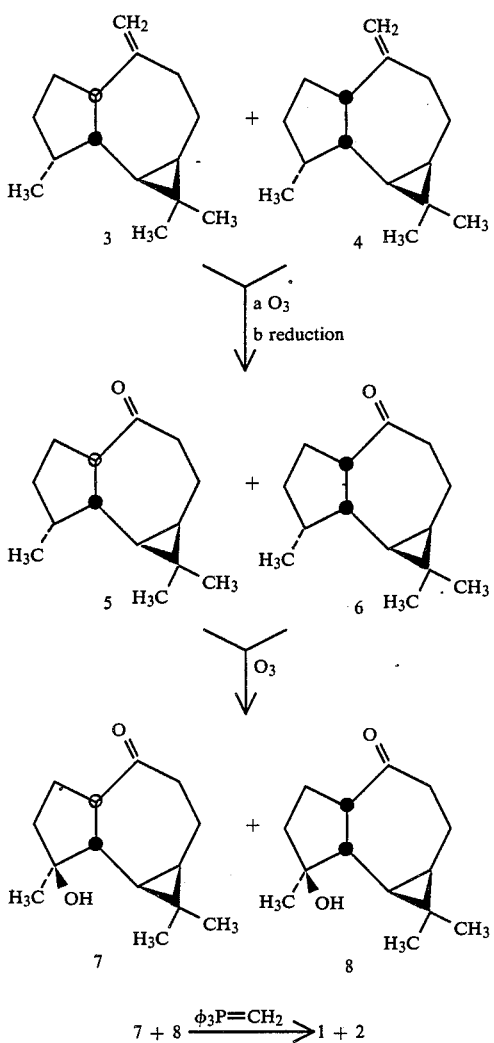

For this purpose, (allo-)aromadendrene (compounds of formulae 3 and 4) is first treated with ozone to form apo-aromadenedranone (compounds of formulae 5 and 6). This reaction can be carried out in, for example, methanol, ethanol or ethyl acetate or in other solvents customary for the ozonisation of double bonds, as described, for example, in Houben-Weyl, Methoden der Organischen Chemie, volume VII-2b, pages 1292–1300 and the literature cited therein. The reaction mixture is worked up reductively in a known manner, for example with the aid of dimethyl sulphide, NaI or catalytic hydrogenation. The ozonisation is preferably carried out at a temperature below 30° C.

The apo-aromadendranone thus obtained in subsequently again treated with ozone, whereby, surprisingly, the compounds having the formulae 7 and 8 are formed in a significant yield. This reaction is preferably carried out in an aprotic solvent such as methylene chloride and at a temperature below 30° C.

This ozonisation can also be carried out after absorption on silica, as described for other compounds by Z. Cohen et al., J. Org. Chem. 40 (1975) 2141–42 and literature cited therein. The two abovementioned reaction steps can also be carried out in a single stage in an aprotic solvent, followed by the reductive working-up already mentioned.

In the hydroxyketones having the formulae 7 and 8, in keto oxygen is finally replaced in a known manner by a methylene group, to form spathulenol, preferably via a Wittig reaction with methylene triphenylphosphorane. This last reaction step is described for (−)-spathulenol in the already mentioned publication by Surburg and Mondon and more generally in H. O. House, Modern Synthetic Reactions (2nd edition), pages 682–709 and literature cited therein.

Starting from (+)-aromadendrene and/or alloaromadendrene (compounds having the formulae 3 and 4), this synthesis route gives a mixture of (+)-spathulenol and (+)-4a-allospathulenol in a ratio of about 5:1. This ratio is independent, or almost independent, of the ratio of aromadendrene to allo-aromadendrene in the starting material, in that under the reaction conditions isomerisation around the carbon atom (4a) occurs in the intermediates of the synthesis route, with formation of an equilibrium amount of trans- and cis-ring-linked products. The other asymmetric centres present in the starting material remain unaffected. By suitable choice of the starting material various stereoisomeric spathulenols can therefore be prepared by the process according to the invention. Thus, (−)-spathulenol together with (−)-4a-allospathulenol can be prepared from (−)-aromadendrene which is isolated from the coral Sinularia mayi (C. Beecham and C. Djerassi, Tetrahedron 34 (1978), 2503–8). The mixture of spathulenol and 4a-allospathulenol obtained by the process according to the invention can be separated into the two components in a simple manner with the aid of column chromatography over silica.

The examples which follow are intended solely to illustrate the process according to the invention and the use of the compounds according to the invention. The invention is, however, not restricted to the embodiment according to the examples.

EXAMPLE I

Preparation of (+)-spathulenol and (+)-4a-allospathulenol a. A solution of 145 g (0.7 mole) of aromadendrene in 500 g of ethanol was cooled to 10° C. and at this temperature an ozone-containing stream of gas was passed through it until in total about 1 mole (48 g) of ozone had been added. Thereafter, 69 g (1.1 moles) of dimethyl sulphide were added at a speed such that the temperature remained below 30° C. The reaction mixture was subsequently warmed slowly under reflux for about 30 minutes. The ethanol was then distilled off under reduced pressure and 300 g of cyclohexane were added to the residue. This mixture was washed three times with water after which the cyclohexane was distilled off under reduced pressure. The residue was distilled under reduced pressure (0.3 kPa), giveing (allo-)apo-aromadendranone in a yield of 130 g (90%).

b. A solution of 130 g of (allo-)apo-aromadendranone in 780 of methylene chloride was cooled to −20° C. An ozone-containing stream of gas was passed through this solution until about 58 g of ozone had been added (about 100% excess), the temperature being kept below −15° C. Thereafter, 400 g of an ice-cold 10% strength KOH solution in water were added to the reaction mixture and the batch was stirred for 1 hour at 0°–5° C. The layers were then separated and the organic (bottom) layer was washed neutral with water. The methylene chloride was distilled off under reduced pressure and the residue was fractionated, 50 g of apo-aromadendranone being recovered (boiling point 100°–140° C./0.7 kPa) and 13 g of hydroxyapo-aromadendranone being obtained (boiling point 160°–175° C./0.7 kPa).

c. 7.2 g of an 80% strength suspension of NaH in oil were mixed with 250 g of dry dimethyl sulphoxide under a nitrogen atomsphere. The mixture was warmed to about 60° C. over the course of 1.5 hours, with continued stirring. After the solution had been cooled to about 25° C., 86 g of triphenylmethylphosphonium bromide (0.24 mole) were added at a speed such that the temperature remained below 35° C. The mixture was stirred for about a further hour at this temperature. Thereafter, a solution of 13 g of hydroxyapo-aromadendranone in 25 g of dry dimethyl sulphoxide was added, again at 35° C. The reaction mixture was stirred for a further 2 hours and then poured into a mixture of 1,000 g of ice and 1,000 g of water. This mixture was subsequently extracted three times with 200 ml of a 1:1 mixture of pentane and ether. The combined extracts were washed with water, dried over sodium sulphate and subsequently evaporated under reduced pressure. A test separation was carried out on a small quantity of the residue by means of thin-layer chromatography over silica, an Rf value of 0.60 being found for (+)-spathulenol and an Rf value of 0.30 for (+)-4a-allospathulenol (elution with a 9:1 pentane/ether mixture).

The entire residue was subsequently purified by column chromatography over silica, using gradient elution with pentane with increasing ether content. The following were obtained successively: 8:5 g of (+)-spathulenol: n 20/D=1.5120; [α]20/D=5° (2% in CHCl₃); NMR (60 MHz, δ in ppm relative to TMS, solvent: CCl₄): 0.40 (1H, dd, J=11 Hz and 9 Hz); 0.7 (1H, m); 1.03 (3H, s); 1.04 (3H, s); 1.21 (3H, s); 1.40 (1H, s, disappears with D₂O); 2.38 (1H, m); 4.60 (2H) and 1.7 g of (+)-4a-allospathulenol: NMR: 0.08 (1H, dd, J=11 Hz and 9 Hz); 0.5 (1H, m); 0.98 (3H, s); 1.01 (3H, s); 1.24 (3H, s); 2.8 (1H, s, disappears with D₂O); 3.0 (1H, m); 4.66 (2H).

The residue can also be purified by distillation under reduced pressure, giving 10.5 g of a 5:1 mixture of (+)-spathulenol and (+)-4a-allospathulenol (boiling point 114°–118° C./0.5 kPa).

The direct yield of the above synthesis, calculated relative to aromadendrene, is 6.5%; if account is taken of the apo-aromadendranone recovered after the second step, the yield is about 11%.

EXAMPLE II

A perfume composition for use in washing powder was prepared in accordance with the following recipe:

| | |
|---|---|
| 5-Acetyl-3-isopropyl-1,1,2,6-tetramethylindane | 130 parts by weight |
| Acetylcedrene | 100 parts by weight |
| γ-Methylionone | 100 parts by weight |
| Tetrahydromyrcenol | 100 parts by weight |
| Tricyclodecenyl acetate | 100 parts by weight |
| Dihydromyrcenol | 80 parts by weight |
| Isononyl acetate | 80 parts by weight |
| Musk xylene | 50 parts by weight |
| Coumarin | 50 parts by weight |
| Benzyl acetate | 50 parts by weight |
| β-phenylethanol | 50 parts by weight |
| Citronellol | 40 parts by weight |
| 2-tert.-Butylcyclohexyl acetate | 30 parts by weight |
| Diphenyl oxide | 20 parts by weight |
| 2-Phenyl-4-methyldihydropyrane | 10 parts by weight |
| α-Ionone | 5 parts by weight |
| Spathulenol mixture of Example I | 5 parts by weight |
| | 1,000 parts by weight |

EXAMPLE III

A flavouring composition (so-called top flavour) for cigarette tabacco was prepared in accordance with the following recipe:

| | |
|---|---|
| Peru balsam | 8.5 parts by weight |
| Tolu balsam | 8.5 parts by weight |
| Styrax resinoid | 8.5 parts by weight |
| Rum ether | 239.0 parts by weight |
| Propylene glycol | 956.6 parts by weight |
| Homogenise the above components well and then add: | |
| Vanillin | 137.5 parts by weight |
| Bulgarian rose oil | 12.5 parts by weight |
| β-Phenylethyl valerate | 4.5 parts by weight |
| Honey flavouring | 4.4 parts by weight |
| Rhodinyl acetate | 2.2 parts by weight |
| Methylphenyl acetate | 2.2 parts by weight |
| Valerian oil | 1.1 parts by weight |
| Lavas oil | 1.1 parts by weight |
| (+)-spathulenol (1% solution in ethanol) | 0.4 part by weight |
| | 10,000 parts by weight |

A 10% solution in ethanol was prepared from the above flavouring composition and was subsequently atomised over cut cigarette tobacco in an amount of 10 g of solution per kg of tobacco. The cigarettes produced from this tobacco had, both in "main stream" and in "side stream", a fuller and richer flavour than cigarettes produced from tobacco flavoured with the same composition *without* spathulenol.

EXAMPLE IV

A flavouring for a blackcurrant liqueur was prepared in accordance with the following recipe:

| | |
|---|---|
| Cassis oil | 2.5 parts by weight |
| Vanillin | 12.5 parts by weight |
| Cinnamon bark oil | 25.0 parts by weight |
| Petitgrain oil | 57.5 parts by weight |
| β-Ionone | 57.5 parts by weight |
| Benzyl acetate | 67.5 parts by weight |
| Ethyl-3-phenyl glycidate | 77.5 parts by weight |
| Ethyl acetate | 600.0 parts by weight |
| Amyl acetate | 600.0 parts by weight |
| Lemon oil | 1,100.0 parts by weight |
| Orange oil | 1,600.0 parts by weight |
| Isobutyl acetate | 2,000.0 parts by weight |
| Amyl butyrate | 2,400.0 parts by weight |
| (+)-Spathulenol (1% solution in ethanol) | 50.0 parts by weight |

A blackcurrant liqueur was prepared with the above flavouring by mixing 300 ml of corn alcohol (96%) and 250 ml of water and then adding 10 g of the above flavouring and 2 g of enocyanine (colorant). The whole was mixed with 350 ml of 62% strength sugar syrup and then made up with water to 1 liter. The liqueur thus obtained had a fuller and more natural blackcurrant flavour than a liqueur prepared with a corresponding flavouring *without* spathulenol.

We claim:

1. A method for the preparation of spathulenol and stereoisomers thereof, comprising
   (a) treating aromadendrene or stereoisomers thereof with ozone to form an intermediate,
   (b) reducing the intermediate to form a keto-compound,
   (c) treating the keto-compound with ozone to form a hydroxy-keto-compound, and
   (d) reacting the hydroxy-keto-compound with methylene triphenylphoshorane to cause a methylene group to be substituted for the keto oxygen.

2. A method according to claim 1, wherein steps (a) and (c) are carried out in an aprotic solvent.

3. A method according to claim 1, wherein step (c) is carried out in an aprotic solvent.

4. A method according to any one of claims 1-3 wherein steps (a)-(c) are carried out after absorbing the aromadendrene on silica.

5. A compound of the formula

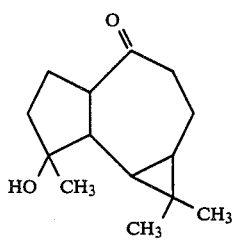

or stereo isomers thereof said compound being prepared by
   (a) treating aromadendrene or stereoisomers thereof with ozone to form an intermediate,
   (b) reducing the intermediate to form a keto-compound,
   (c) treating the keto-compound with ozone to form a hydroxy-keto-compound, and
   (d) reacting the hydroxy-keto-compound with methylene triphenylphosphorane to cause a methylene group to be substituted for the keto oxygen.

6. Flavouring and perfume compositions comprising a compound of the formula

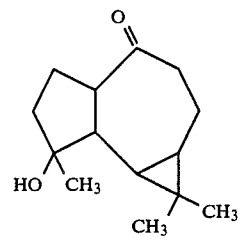

or stereoisomers thereof, said compound being prepared by
   (a) treating aromadendrene or stereoisomers thereof with ozone to form an intermediate,
   (b) reducing the intermediate to form a keto-compound,
   (c) treating the keto-compound with ozone to form a hydroxy-keto-compound, and
   (d) reacting the hydroxy-keto-compound with methylene triphenylphosphorane to cause a methylene group to be substituted for the keto oxygen, said compound being present at levels of at least 1 part per million; and
suitable carriers or diluents.

7. Articles containing a compound of the formula

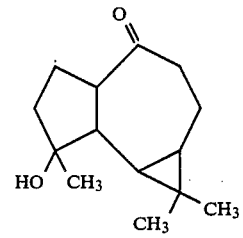

or stereoisomers thereof, said compound being prepared by
   (a) treating aromadendrene or stereoisomers thereof with ozone to form an intermediate,
   (b) reducing the intermediate to form a keto-compound,
   (c) treating the keto-compound with ozone to form a hydroxy-keto-compound, and
   (d) reacting the hydroxy-keto-compound with methylene triphenylphosphorane to cause a methylene group to be substituted for the keto oxygen; and
suitable carriers or diluents, said compound being present at levels of at least 0.1 parts by weight per billion; and said articles being selected from the group consisting of flavored foodstuffs, luxury consumables, and perfumed products.

8. A method of imparting dry woody odor to an article comprising treating the article with a compound of the formula

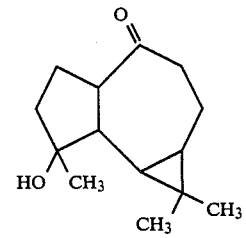

or stereoisomers thereof said compound being prepared by
(a) treating aromadendrene or stereoisomers thereof with ozone to form an intermediate,
(b) reducing the intermediate to form a keto-compound,
(c) treating the keto-compound with ozone to form a hydroxy-keto-compound, and
(d) reacting the hydroxy-keto-compound with methylene triphenylphosphorane to cause a methylene group to be substituted for the keto oxygen, said article being treated with an amount of the compound such that the article retains an organoleptically acceptable amount of the compound.

9. A method of imparting a cassia-like flavor to foodstuffs and luxury consumables comprising adding to the foodstuffs and luxury consumables a compound of the formula

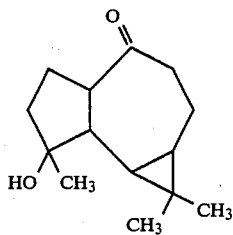

or stereoisomers thereof, said compound being prepared by
(a) treating aromadendrene or stereoisomers thereof with ozone to form an intermediate,
(b) reducing the intermediate to form a keto-compound,
(c) treating the keto-compound with ozone to form a hydroxy-keto-compound, and
(d) reacting the hydroxy-keto-compound with methylene triphenylphosphorane to cause a methylene group to be substituted for the keto oxygen, said compound being added in an amount sufficient to achieve an organoleptically acceptable result.

10. A method for preparing flavoring compositions comprising add to conventional flavoring components an effective flavouring amount of substantially pure (+)-spathulenol, (+)-4a-allospathulenol, or a mixture thereof.

11. A method for preparing flavored foodstuffs comprising adding to said foodstuffs at least 0.1 parts per billion by weight of substantially pure (+)-spathulenol, (+)-4a-allospathulenol, or a mixture thereof.

12. A method for preparing perfume compositions comprising adding to conventional perfume components an effective odorant amount of substantially pure (+)-spathulenol, (+)-4a-allospathulenol, or a mixture thereof.

13. A method according to claim 12, wherein at least 1 part per million by weight of substantially pure (+)-spathulenol, (+)-4a-allospathulenol, or a mixture thereof is added.

* * * * *

UNITED STATES PATENT AND TRADEMARK OFFICE
CERTIFICATE OF CORRECTION

PATENT NO. : 4,704,232

DATED : November 3, 1987

INVENTOR(S) : van der Linde et al.

It is certified that error appears in the above-identified patent and that said Letters Patent is hereby corrected as shown below:

First page, Item 73, "Ussum" should read --Naarden-Bussum--;

First page, penultimate line of ABSTRACT, after "material" insert comma;

Column 1, line 63, "118'130" should read --118-130--;

Column 2, line 55, after "in" delete "the";

Column 3, line 60, "apo-aromadenedranone" should read --apo-aromadendranone--;

Column 4, line 17, "in keto" should read --the keto--;

UNITED STATES PATENT AND TRADEMARK OFFICE
CERTIFICATE OF CORRECTION

PATENT NO. : 4,704,232

DATED : November 3, 1987

INVENTOR(S) : van der Linde et al.

It is certified that error appears in the above-identified patent and that said Letters Patent is hereby corrected as shown below:

Column 7, line 45, that portion of the formula reading "O" should read --$CH_2$--;

Column 8, line 1, that portion of the formula reading "O" should read --$CH_2$--;

Column 8, line 30, that portion of the formula reading "O" should read --$CH_2$--;

Column 8, line 60, that portion of the formula reading "O" should read --$CH_2$--;

Column 9, line 25, that portion of the formula reading "O" should read --$CH_2$--;

Column 10, line 15, "add" should read --adding--;

Signed and Sealed this

Twenty-seventh Day of September, 1988

Attest:

DONALD J. QUIGG

Attesting Officer

Commissioner of Patents and Trademarks